(12) United States Patent
Holstein

(10) Patent No.: US 11,065,074 B2
(45) Date of Patent: Jul. 20, 2021

(54) EASY ACCESS BANDAGES

(71) Applicant: Genuine First Aid International Ltd., Kowloon (HK)

(72) Inventor: Michael Holstein, Clearwater, FL (US)

(73) Assignee: Genuine First Aid International Ltd., Kowloon (HK)

(*) Notice: Subject to any disclaimer, the term of this patent is extended or adjusted under 35 U.S.C. 154(b) by 0 days.

(21) Appl. No.: 16/446,321

(22) Filed: Jun. 19, 2019

(65) Prior Publication Data
US 2019/0298475 A1 Oct. 3, 2019

Related U.S. Application Data

(63) Continuation-in-part of application No. 15/618,006, filed on Jun. 8, 2017, now abandoned.

(60) Provisional application No. 62/348,079, filed on Jun. 9, 2016.

(51) Int. Cl.
  *A61B 50/31* (2016.01)
  *A61F 17/00* (2006.01)
  *A61B 50/30* (2016.01)

(52) U.S. Cl.
  CPC ............ *A61B 50/312* (2016.02); *A61F 17/00* (2013.01); *A61B 2050/3008* (2016.02); *A61B 2050/311* (2016.02)

(58) Field of Classification Search
  CPC .......... A61B 50/312; A61B 2050/3008; A61B 2050/311; A61B 2050/3011; A61F 17/00; A61F 13/00072; A61F 13/00076; A61F 13/0008; A61F 13/00085; A61F 13/005; A61F 13/0259; A45C 13/12

USPC .......... 206/570, 440, 441, 477, 482
  See application file for complete search history.

(56) References Cited

U.S. PATENT DOCUMENTS

| | | | | |
|---|---|---|---|---|
| 3,677,866 A * | 7/1972 | Pickett | .................. | B65D 83/00 206/306 |
| 4,194,624 A * | 3/1980 | Spiegelberg | ........... | B65D 83/08 206/441 |
| 6,050,413 A * | 4/2000 | Benedetti | .............. | A61F 15/001 206/440 |
| 6,708,826 B1 * | 3/2004 | Ginsberg | ............. | B65D 33/001 206/425 |
| 7,188,729 B2 * | 3/2007 | DeJonge | ............ | B65D 83/0463 206/1.5 |
| 7,762,635 B2 * | 7/2010 | Spoljaric | ................ | A47B 67/02 312/291 |
| 8,220,636 B2 * | 7/2012 | Beecroft | ............ | B65D 83/0472 206/1.5 |

(Continued)

*Primary Examiner* — J. Gregory Pickett
*Assistant Examiner* — Jenine Pagan
(74) *Attorney, Agent, or Firm* — Nicholas Pfeifer; Smith & Hopen, P. A.

(57) ABSTRACT

A medical supply case or cabinet is provided having a case body. A first hinged door is providing access to a first compartment residing within the case body. A retaining mechanism has a peg spaced apart from the first hinged door such that the peg may receive an aperture of the first medical item when in a first configuration. When the retaining mechanism is in the second configuration the peg remains disposed through the aperture of the first medical item which is secured between the first hinged door and a securing member. The medical supply case can include a second hinged door that provides access to a second compartment. Additionally, the first hinged door may reside within the second hinged door.

14 Claims, 9 Drawing Sheets

(56) References Cited

U.S. PATENT DOCUMENTS

| | | | |
|---|---|---|---|
| 8,708,149 B2* | 4/2014 | Hawry | B65D 25/10 |
| | | | 206/535 |
| 8,944,247 B2* | 2/2015 | Hackbarth | A61F 15/001 |
| | | | 206/440 |
| 9,254,229 B2* | 2/2016 | Barkholt | A61F 15/002 |
| 2014/0034648 A1* | 2/2014 | Peterson | A61F 17/00 |
| | | | 220/507 |

* cited by examiner

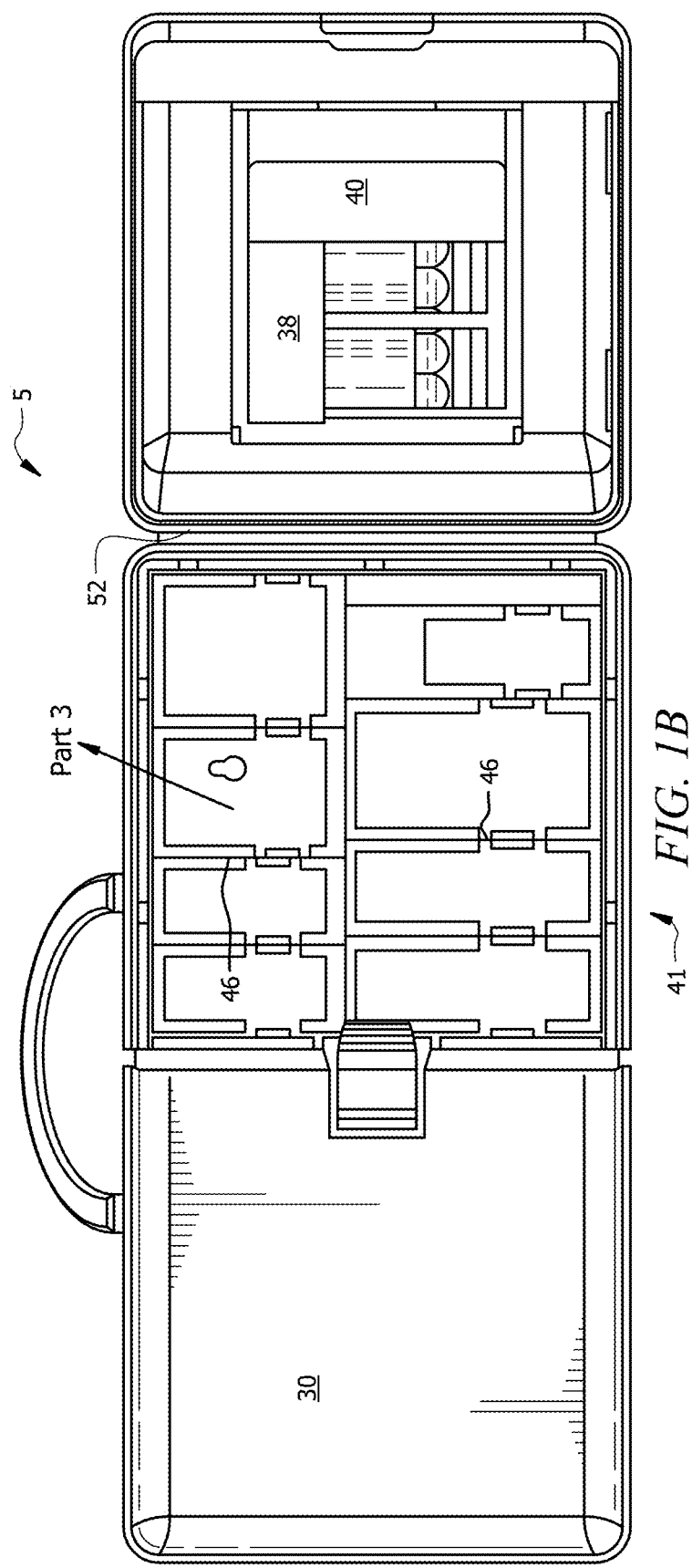

EASY ACCESS BANDAGES

CROSS-REFERENCE TO RELATED APPLICATIONS

This non-provisional application is a continuation-in-part ("CIP") of and claims priority to non-provisional application Ser. No. 15/618,006, entitled "EASY ACCESS BANDAGES CASE," filed Jun. 8, 2017, which claims priority to provisional application No. 62/348,079, entitled "EASY ACCESS BANDAGES CASE," filed Jun. 9, 2016 by the same inventor, the entireties of which are incorporated herein by reference.

BACKGROUND OF THE INVENTION

1. Field of the Invention

This invention relates, generally, to medical supply cases. More specifically, it relates to medical supply cases capable of providing rapid access to medical items.

2. Brief Description of the Prior Art

A wound must be covered as soon as possible after injury to prevent bacteria from entering the body and causing further harm by infection. One of the most troublesome issues in dealing with injuries is the possibility of an infection or secondary infection. Secondary infections are caused by bacteria entering the wound at any time after the initial injury. Even if the original injury already caused an infection, harm caused by secondary infections can be avoided through proper cleaning and rapid application of bandages to cover the wound. According to the World Health Organization ("WHO"), bandages provide not only a moist environment to promote skin cell recovery, but also serve to reduce instances of infection by outside bacteria.

Bandages are the most widely used medical items for covering wounds such as punctures, scrapes, scratches, or cuts prevent infection by outside bacteria. Of course, if bandages are not readily available or easily accessible, precious time can be lost with an exposed injury. Traditional bandage packaging and storage requires extensive manipulation, using two hands, to prepare the bandage for application.

Existing medical supply cases are often not configured for quick access. Other bandage application systems require a consumer to open a medical supply case and then rip and tear the bandage packaging apart to gain access to an adhesive bandage, which is slow and inconvenient.

Accordingly, what is needed is a medical supply case that allows rapid access to medical items including sterile bandages, with one hand in a ready-to-apply-state. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a medical supply case that is capable of utilizing a bandage application system is now met by a new, useful, and non-obvious invention.

The novel structure includes a case body with a first hinged door that provides access to a first compartment residing within the case body. A retaining assembly has a first configuration in which the securing member is spaced apart from the first hinged door such that the first medical supply can be received between the securing member and the first hinged door. In a second configuration, the first medical item can be secured between the securing member and the first hinged door preventing the lateral movement of the first medical item. The first medical item has a first end opposite a second end, with the second end being detachable from the first end when pulled away from the first end of the medical item, resulting in the second end dissociating from the first end which remains secured in the second configuration.

The first hinged door may also include a peg having a first end and a second end. The first end of the peg abuts the first hinged door and is opposite the second end of the peg which is in mechanical communication with the securing member when in the second configuration. The peg is spaced apart from the first hinged door such that the peg can receive an aperture of the first medical item when in a first configuration. In the second configuration, the securing member secures the first medical item between the securing member and the first hinged door such that the peg remains disposed through the aperture of the first medical item when in the second configuration.

The securing member further includes a receipt configured to receive a portion of the peg so that then the peg and the securing member are in mechanical communication with one another the peg resides within the receipt and is partially secured within the receipt.

In an embodiment, the second hinged door provides access to a second compartment residing within the case body. In an embodiment, a third compartment resides within the case body and inaccessible via the first hinged door. In an embodiment, a third compartment resides within the case body and is accessible via the first hinged door. In an embodiment, the first medical item includes an individual sterile adhesive bandage, a first wrapper element, and a second wrapper element. The first wrapper element and the second wrapper element at least partially enclose the bandage and are different sizes and contain an unequal portion of the bandage. Either the first wrapper element or the second wrapper element is attached to the associated protection paper. In an embodiment, the first medical item includes an aperture.

In an embodiment the medical supply cases comprises a case body, a first hinged door and a second hinged door disposed on a surface of the case body, a handle protruding from a surface of the case body, a first compartment mounted on an inside of the case body accessible via the first hinged door and a second compartment mounted on an inside of the case body accessible via the second hinged door, a third compartment mounted on an inside of the case body inaccessible via the first hinged door and the second hinged door; and a clasp for securing the case body in a closed state. In some embodiments, the first hinged door and the second hinged door are of unequal sizes. In some embodiments, the case body comprises hinges disposed on a surface. In some embodiments, the hinges are disposed on the bottom surface of a case. In some embodiments, the hinges are disposed on the left and/or the right surface of a case. In some embodiments, the first compartment contains a first medical item and the second compartment contains a second medical item. In some embodiments, the second medical item is eyewash.

In some embodiments, the medical supply cases and cabinets described herein contain a first medical item. In some embodiments, the first medical item is a bandage application system. In some embodiments, the bandage application system comprises an individual sterile adhesive bandage, a first wrapper element, and a second wrapper element. In some embodiments, the first wrapper element and the second wrapper element at least partially enclose the bandage and are different sizes and contain unequal portions of the bandage. In some embodiments, either the first wrapper element or the second wrapper element is attached to an associated protection paper.

In some embodiments, the medical supply cases and cabinets described herein contain a bandage application system. In another embodiment, the bandage application system comprises an individual sterile adhesive bandage comprising a backing, at least one absorbent patch, and two adhesive regions, wherein adhesive is applied to the backing, and each adhesive region has an overlaying protection paper. In some embodiments, the bandage application system further comprises a first wrapper element and a second wrapper element, whereby the first wrapper element and the second wrapper element at least partially enclose the bandage and are separably in contact to completely enclose the bandage such that when the first and second wrapper elements are pulled in opposite directions the first and second elements do not require ripping or tearing to separate to partially expose the bandage in a ready-to-apply state and said partially exposed bandage remains associated with one of the wrapper elements and the other wrapper elements dissociates from said bandage, and wherein only one of the two protection papers is attached to an associated wrapper element.

In some embodiments, the case body is hard-sided and made of plastic. In some embodiments, the case body is soft-sided and made of water-resistant material. In some embodiments, the case body measures at least 10 centimeters by 10 centimeters on one surface. In some embodiments, the case body measures at most 3 meters by 3 meters on one surface. In some embodiments, the case contains between 1 and 100 additional compartments (such as partitions within individual compartments, or additional compartments beyond the first compartment, second compartment, and third compartment described above). In some embodiments, the first compartment measures at least 9.5 centimeters by 10.8 centimeters by 1 centimeter. In some embodiments, the first compartment contains a peg for mounting the bandage application system. In some embodiments, the peg has a radius of approximately 2.5 millimeters. In some embodiments, the case contains two pegs approximately 4.8 centimeters apart from each other. In some embodiments, the second compartment measures at least 3 centimeters by 12.5 centimeters by 3.2 centimeters. In some embodiments, the second compartment measures at least 4 centimeters by 13 centimeters by 5.1 centimeters. In some embodiments, the handle comprises a cut out for wall mounting the case. In some embodiments, the case body comprises a cut out for wall mounting the case. In some embodiments, the clasp is lockable. In some embodiments, the case body is bi-fold and hinged on a surface opposite the handle. In some embodiments, the case comprises two clasps for securing the case body in a closed state. In some embodiments, the case contains a plurality of alcohol cleansing pads. In some embodiments, the case contains a plurality of antiseptic towelettes. In some embodiments, the case contains one or more packets of burn cream. In some embodiments, the case contains one or more packets of triple antibiotic ointment. In some embodiments, the case contains a plurality of povidone-iodine prep pads. In some embodiments, the case contains one or more packets of hydrocortisone cream. In some embodiments, the case contains one or more packets of hand sanitizer. In some embodiments, the case contains a plurality of insect sting relief pads.

In some embodiments, the additional compartments of the cases described herein contain medical supplies. In some embodiments, the additional compartments contain a first aid guide that provides instructions for identification and initial care of injury and illness. In some embodiments, additional compartments contain a CPR breathing barrier. In some embodiments, additional compartments contain one or more sterile dressings. In some embodiments, additional compartments contain one or more pairs of disposable gloves. In some embodiments, additional compartments contain one or more bandages. In some embodiments, additional compartments contain a plurality of aspirin. In some embodiments, additional compartments contain one or more roller bandages. In some embodiments, additional compartments contain one or more sterile gauze pads. In some embodiments, additional compartments contain a triangular bandage. In some embodiments, additional compartments contain one or more sterile eye pads, one or more vials of sterile eye wash, and a plurality of butterfly wound closures. In some embodiments, additional compartments contain a roll of first aid tape. In some embodiments, additional compartments contain a plurality of safety pins. In some embodiments, additional compartments contain an emergency blanket and a cold pack. In some embodiments, additional compartments contain a pair of tweezers. In some embodiments, additional compartments contain a pair of scissors and a plurality of wooden finger splints. In some embodiments, additional compartments contain a face mask, an emergency poncho, a whistle, a light stick, and an emergency radio/flashlight. In some embodiments, additional compartments contain a plurality of batteries.

In another aspect, disclosed herein are medical supply cases comprising a first compartment containing a bandage application system comprising: an individual sterile adhesive bandage; a first wrapper element; and a second wrapper element; whereby the first wrapper element and the second wrapper element at least partially enclose the bandage and are separably in contact to completely enclose the bandage such that when the first and second wrapper elements are pulled in opposite directions the first and second elements separate to partially expose the bandage in a ready-to-apply state. In some embodiments, the first and second wrapper elements each comprise two parallel sheets sealed on three of four sides. In some embodiments, the bandage, when in a ready-to-apply state, is characterized by having at least one exposed adhesive area in a condition to adhere to skin. In some embodiments, the first and second wrapper elements are each printed to indicate an appropriate grip area. In some embodiments, the first and second wrapper elements are printed with bandage application instructions. In some embodiments, the first and second wrapper elements are separably in contact via a perforated, scored, or overlapping region. In some embodiments, upon separation of the first and second wrapper elements, the partially exposed bandage remains associated with either the first or the second wrapper element. In some embodiments, separation of the first and second wrapper elements does not require ripping or tearing of either the first or the second wrapper element. In some embodiments, the bandage comprises: a backing; at least one absorbent region; at least one adhesive region, wherein adhesive is applied to the backing; and a protection paper overlaying each adhesive region. In further embodiments, upon separation of the first and second wrapper elements, at least one protection paper remains associated with either the first or the second wrapper element, thereby exposing the adhesive. In some embodiments, the bandage is a strip bandage about 76 mm long and about 25 mm wide. In some embodiments, the bandage is a strip bandage about 76 mm long and about 19 mm wide. In some embodiments, the bandage is a strip bandage about 40 mm long and about 10 mm wide, in some embodiments, the bandage is a knuckle bandage about 76 mm long and about 38 mm wide. In some embodiments, the bandage is a fingertip bandage about 51 mm long and about 45 mm wide. In various embodiments, the bandage is a plastic bandage, a fabric bandage, a metal detectable bandage, or a combination thereof. In some embodiments, the bandage is medicated. In other embodiments, the bandage is non-medicated.

In another aspect, disclosed herein is a medical supply case, the case having about 5 to about 100 of the bandage application systems disposed therein. In some embodiments, the container has about 20 of the bandage application systems disposed therein.

In another aspect, disclosed herein are medical supply cases comprising a first compartment containing a bandage application systems comprising: an individual sterile adhesive bandage; a first wrapper element; and a second wrapper element; the first and second wrapper elements each comprising two parallel sheets sealed on three of four sides to form a pocket, the first wrapper element and the second wrapper element at least partially enclosing the bandage in respective pockets, and the first wrapper element and the second wrapper element separably in contact to completely enclose the bandage. In some embodiments, the first and second wrapper elements are each printed to indicate an appropriate grip area. In some embodiments, the first and second wrapper elements are printed with bandage application instructions. In some embodiments, the first and second wrapper elements are separably in contact via a perforated, scored, or overlapping region. In some embodiments, upon separation of the first and second wrapper elements, the partially exposed bandage remains associated with either the first or the second wrapper element. In some embodiments, separation of the first and second wrapper elements does not require ripping or tearing of either the first or the second wrapper element. In some embodiments, the bandage is a strip bandage about 76 mm long and about 25 mm wide. In some embodiments, the bandage is a strip bandage about 76 mm long and about 19 mm wide. In some embodiments, the bandage is a strip bandage about 40 mm long and about 10 mm wide. In some embodiments, the bandage is a knuckle bandage about 76 mm long and about 38 mm wide. In some embodiments, the bandage is a fingertip bandage about 51 mm long and about 45 mm wide. In various embodiments, the bandage is a plastic bandage, a fabric bandage, a metal detectable bandage, or a combination thereof. In some embodiments, the bandage is medicated. In other embodiments, the bandage is non-medicated. In some embodiments, when the first and second wrapper elements are pulled in opposite directions the first and second elements separate to partially expose the bandage in a ready-to-apply state. In further embodiments, the bandage, when in a ready-to-apply state, is characterized by having at least one exposed adhesive area in a condition to adhere to skin. In some embodiments, the bandage comprises: a backing; at least one absorbent region; at least one adhesive region, wherein adhesive is applied to the backing; and a protection paper overlaying each adhesive region. In still further embodiments, upon separation of the first and second wrapper elements, at least one protection paper remains associated with a wrapper element, thereby exposing the adhesive.

In another aspect, disclosed herein are medical supply cases containing a bandage application system comprising individual wrappers for an adhesive bandage, the wrapper comprising: a first wrapper element; and a second wrapper element; the first and second wrapper elements each comprising two parallel sheets sealed on three of four sides, the first and second wrapper elements separably in contact to form an interior adapted to completely enclose an individual adhesive bandage; provided that when the first and second wrapper elements are gripped and pulled in opposite directions the first and second elements separate to partially expose a bandage disposed in the interior in a ready-to-apply state. In some embodiments, the first and second wrapper elements are each printed to indicate an appropriate grip area. In some embodiments, the first and second wrapper elements are printed with bandage application instructions. In some embodiments, the first and second wrapper elements are separably in contact via a perforated, scored, or overlapping region. In some embodiments, upon separation of the first and second wrapper elements, a partially exposed bandage remains associated with either the first or the second wrapper element. In some embodiments, separation of the first and second wrapper elements does not require ripping or tearing of either the first or the second wrapper element. In some embodiments, the individual adhesive bandage comprises at least one adhesive region and a protection paper overlaying each adhesive region; wherein upon separation of the first and second wrapper elements, the at least one protection paper remains associated with either the first or the second wrapper element, thereby exposing the adhesive.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 1B depicts the medical supply case with the case body in a partially open configuration. The first compartment containing a bandage application system and the second compartment are visible. There are approximately nine partitions disposed within the inside of the case body that are visible in the embodiment depicted in FIG. 1B.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

Described herein are medical supply cases configured to allow rapid access to medical items stored in the case. In one embodiment, described herein is a medical supply case comprising a case body, a first hinged door and a second hinged door disposed on a surface of the case body, a handle protruding from a surface of the case body, a first compartment mounted on an inside of the case accessible via the first hinged door and a second compartment mounted on an inside of the case body accessible via the second hinged door, a third compartment mounted on an inside of the case body inaccessible via the first hinged door and the second hinged door, and a clasp for securing the case body in a closed state, wherein the first hinged door and the second hinged door are unequal sizes, wherein the case body comprises hinges disposed on a surface, and wherein the first compartment contains a first medical item and the second compartment contains a second medical item. In some embodiments, the second medical item is different than the first medical item. In some embodiments, the second medical item is the same as the first medical item. In some embodiments, the second medical item is eye wash. In some embodiments, the first medical item is a bandage application system, such as a bandage application system comprising individual bandages and bandage wrappers that allow efficient removal of the bandage from its packaging mounted inside the medical supply case in a ready-to-apply state, which facilitates rapid application of the bandage and lowers the risk of the bandage becoming contaminated through excessive handling. In some embodiments, the cases, bandage application systems, individual bandages, and bandage wrappers described herein allow for rapid removal of the bandage wrapper with only one hand and thus reduce the potential for user introduced bacteria and secondary infection.

Figure 1A:
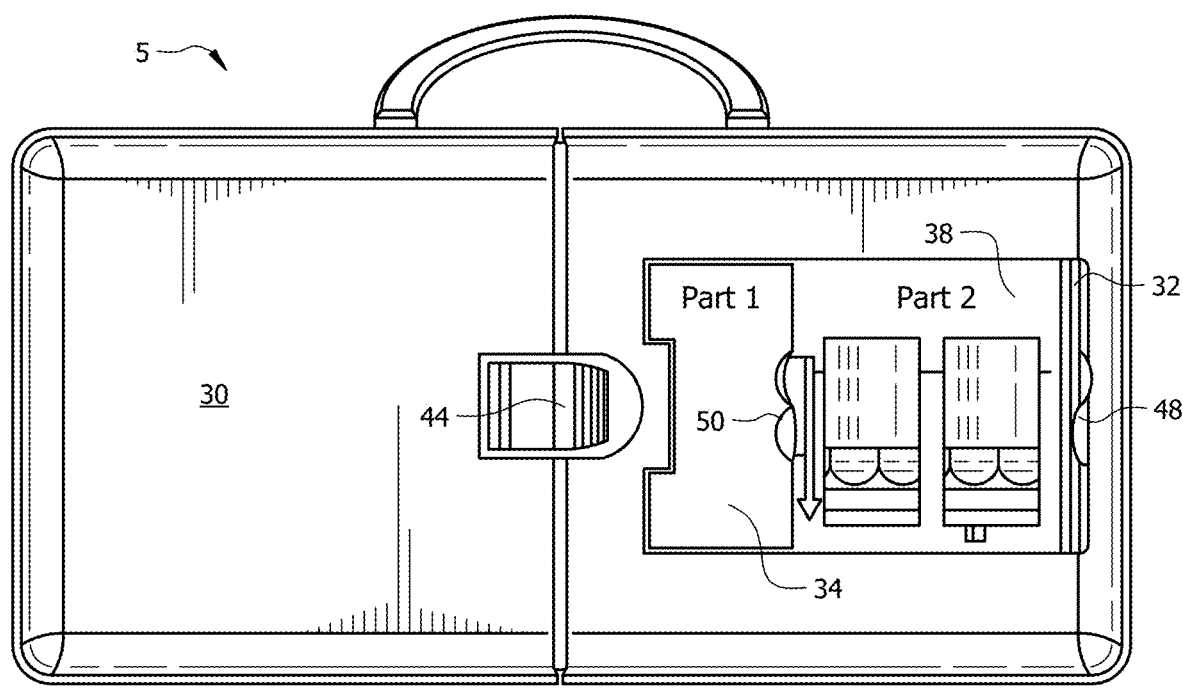
FIG. 1A depicts a non-limiting example of a medical supply case with the case body in a closed configuration, the first hinged door in an open configuration; and the second hinged door in a closed configuration. The first compartment containing a bandage application system is visible.

Referring to FIG. 1A, in a particular embodiment, shown in a closed configuration is a medical supply case 5 with a case body 30. In this embodiment, the case includes a first hinged door 32 in an open configuration, allowing access to a first compartment 38 containing a bandage application system. The case also includes second hinged door 34 which is shown in a closed configuration, rendering the second compartment not visible. The first hinged door may contain a raised portion 48 to allow a user to quickly open the first hinged door 32. Second hinged door 34 may contain a raised portion 50 to allow a user to quickly open second hinged door 34. As shown in FIG. 1A, the raised portions 48, 50 may align with an indentation on the opposite door.

The arrow in FIG. 1A indicates the direction a user will pull on a bandage in order to remove it from the bandage application system. In some embodiments, the bandage application system is an Easy Access Bandage™ and when a user needs a bandage, the user just pulls down on the bandage in the direction of the arrow. Medical supply case 5 may also include clasp 44, which secures case body 30 in a closed configuration. Clasp 44 may be lockable, or it may be relatively easy to open. Clasp 44 may also be a push button, a slide lever, or the like. Undoing clasp 44 allows a user to open the medical supply case 5 and access third compartment 41, as shown in FIG. 1B.

FIG. 1B depicts the medical supply case 5 with case body 30 in a partially open configuration. Medical supply case 5 opens by way of hinge 52 disposed on the right- and left-handed sides of case body 30. As shown in FIG. 1B, medical supply case 5 opens to reveal at least a portion of third compartment 41—in FIG. 1B, the portion of third compartment 41 visible is the right-hand side of third compartment 41. First compartment 38 containing a bandage application system and second compartment 40 are visible. In some embodiments, second compartment 40 contains a second medical item. In some embodiments, the second medical item is the same as the first medical item located in first compartment 38. In some embodiments, the second medical item is different than the first medical item located in first compartment 38. In some embodiments, the second medical item is eyewash. In some embodiments, the eyewash is a vial of eyewash. In some embodiments, the eyewash is a bottle of eyewash. The size of the eyewash will vary based on need and configuration. In some embodiments, the eyewash is 1, 2, 3, 4, 5, 6, 7, 8, 9, 10, 11, 12, 13, 14, 15, or 16 ounces. In some embodiments, the eyewash is 16, 32, 48, or 64 ounces. In some embodiments, the eyewash is affixed to the medical supply case. In some embodiments, the eyewash is removable from the medical supply case.

Figure 1C:
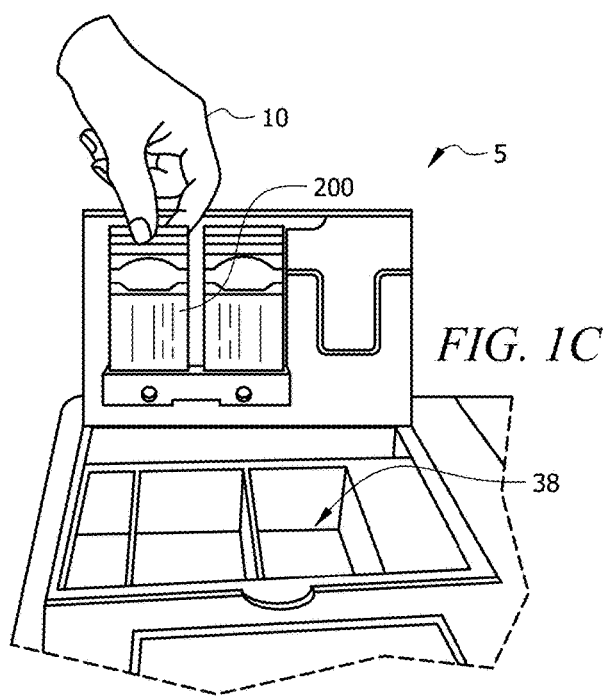
FIG. 1C depicts a non-limiting example of a medical supply case in which a user firmly grips the bandage tab.
Figure 1D:
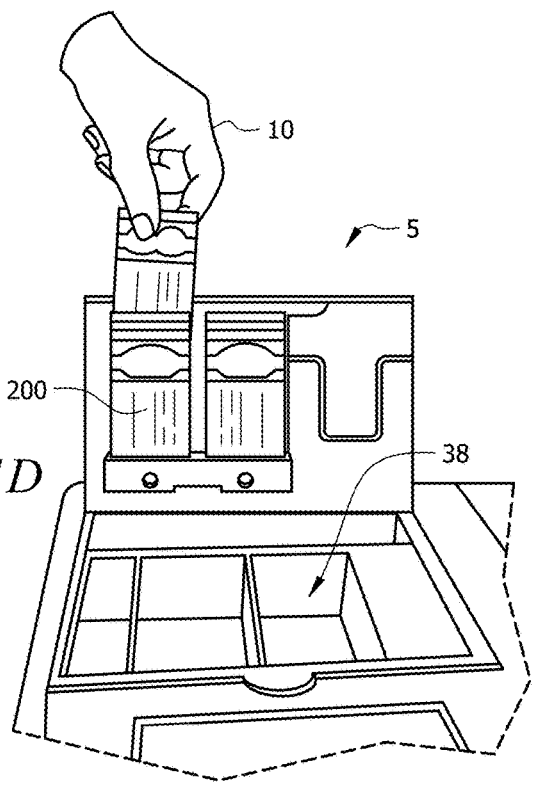
FIG. 1D depicts a non-limiting example of a medical supply case in which a user pulls the bandage straight out from the first hinged door.
Figure 1E:
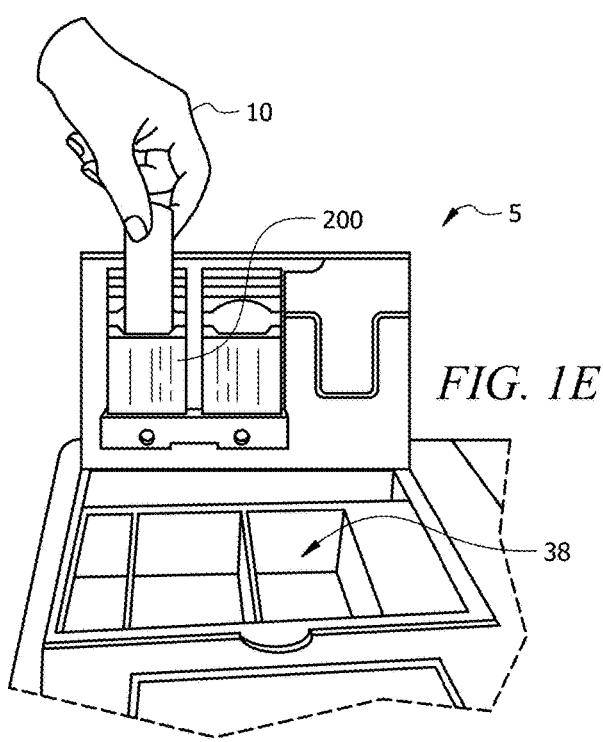
FIG. 1E depicts a non-limiting example of a medical supply case in which the bandage adhesive side is exposed leaving the wrapper behind in the container.
Figure 1F:
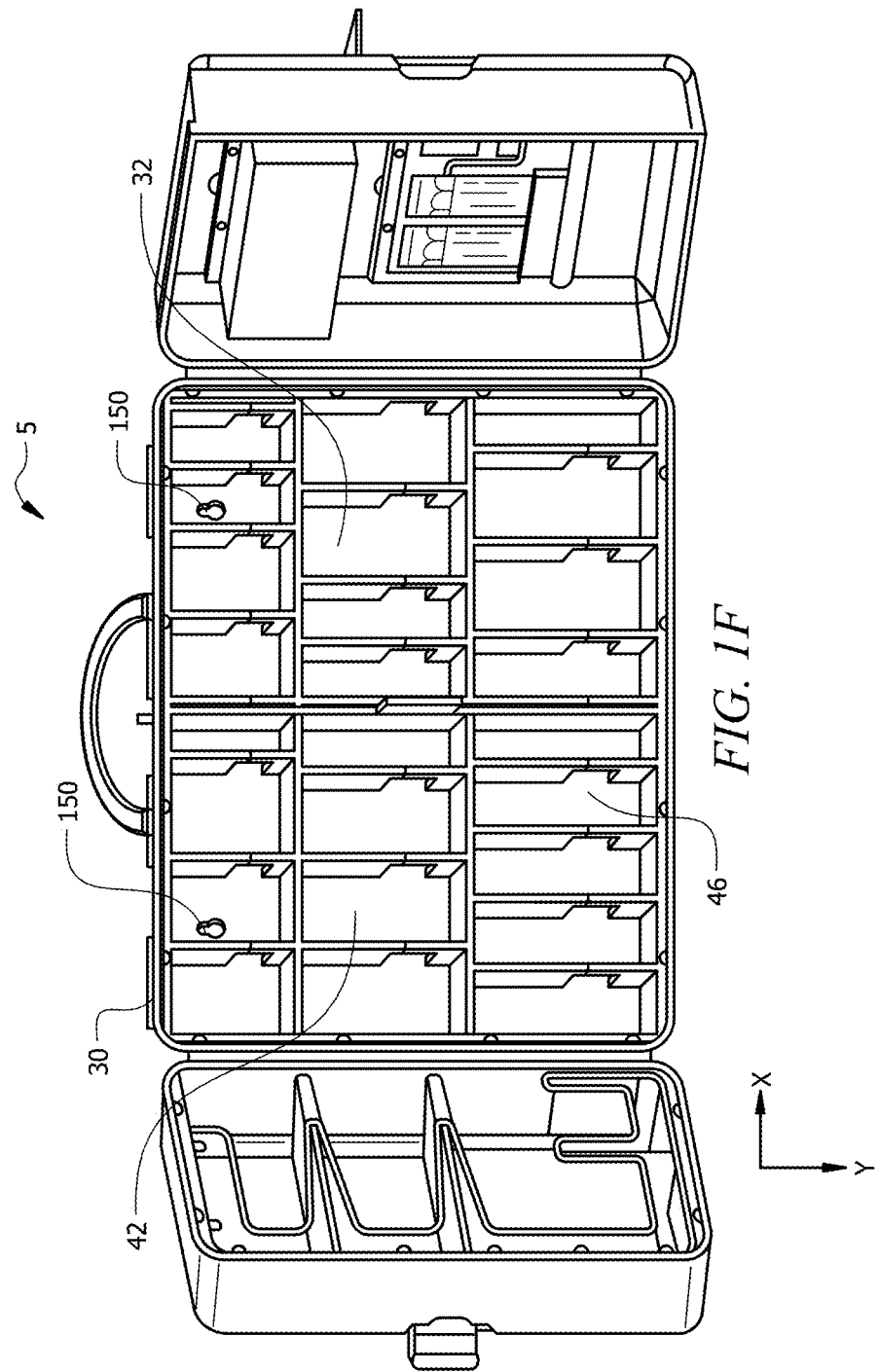
FIG. 1F depicts a non-limiting example of a medical supply case with the case body in a fully open configuration.

As shown in FIG. 1B, medical case 5 is configured to contain a plurality of compartments, which can be further divided into partitions. For example, as shown in FIG. 1B, third compartment 41 includes approximately nine partitions, such as partition 42 and partition 46. Additional partitions may be located on the left-hand side of third compartment 41 disposed within the inside of the case body 30, as shown in FIG. 1F. However, the number of partitions can vary according to need and configuration. In some embodiments, medical supply case or cabinet 5 comprises 1, 2, 3, 4, 5, 6, 7, 8, 9, 10, 11, 12, 13, 14, 15, 16, 17, 18, 19, 20, 25, 30, 35, 40, 45, 50, 60, 70, 80, or 90 partitions. In some embodiments, the number of partitions is any number between 1 and 100 partitions. In some embodiments, medical supply case or cabinet 5 comprises 100, 110, 120, 130, 140, or 150 partitions. Partitions may be configured to be any shape or size. Partitions may be configured to securely receive and secure various medical supplies. In some embodiments, can easily be removed and replaced when refill of the medical supplies is needed. FIGS. 1C through 1E depict an embodiment of medical supply case 5 in which a user 10 firmly grips the first medical item 200 using just one hand from first compartment 38. The figures depict the user 10 applying a force away from the first end of the bandage and pulling the bandage straight out by the second end of the bandage, such that the second end of the bandage dissociates from medical supply case 5 in a ready-to-apply configuration with the adhesive side exposed and the wrapper pulled away.

The third compartment 41, and more specifically partitions, of the cases described herein are particularly useful for organizing and securing medical supplies. Medical supplies include supplies useful for the treatment of small cuts and burns, medium cuts and scratches, and severe bleeding and burns. Medical supplies also include supplies useful for emergency preparedness, CPR, disease and injury protection, and instruments. In some embodiments, the third compartment 41 contains one or more of an eye wash, a bandage application system, a plurality of alcohol cleansing pads, a plurality of antiseptic towelettes, one or more packets of burn cream, one or more packets of triple antibiotic ointment, a plurality of povidone-iodine prep pads, one or more packets of hydrocortisone cream, one or more packets of hand sanitizer, a plurality of insect sting relief pads, a first aid guide that provides instructions for identification and initial care of injury and illness, a CPR breathing barrier, one or more sterile dressings, one or more pairs of disposable gloves, one or more bandages, a plurality of aspirin, one or more roller bandages, one or more sterile gauze pads, a triangular bandage, one or more sterile eye pads, one or more vials of sterile eye wash, and a plurality of butterfly wound closures, a roll of first aid tape, a plurality of safety pins, an emergency blanket and a cold pack, a pair of tweezers, a pair of scissors and a plurality of wooden finger splints, a face mask, an emergency poncho, a whistle, a light stick, and an emergency radio/flashlight, and a plurality of batteries.

Referring to FIG. 1F, in a particular embodiment, depicted is a cutaway drawing of a non-limiting example of a medical supply case in an open configuration. Case 5 includes cutout 150 for mounting the bandage application system. In an embodiment, cutout 150 has a radius of approximately 2.5 millimeters. Two cutouts 150 are visible in FIG. 1F.

Figure 2:
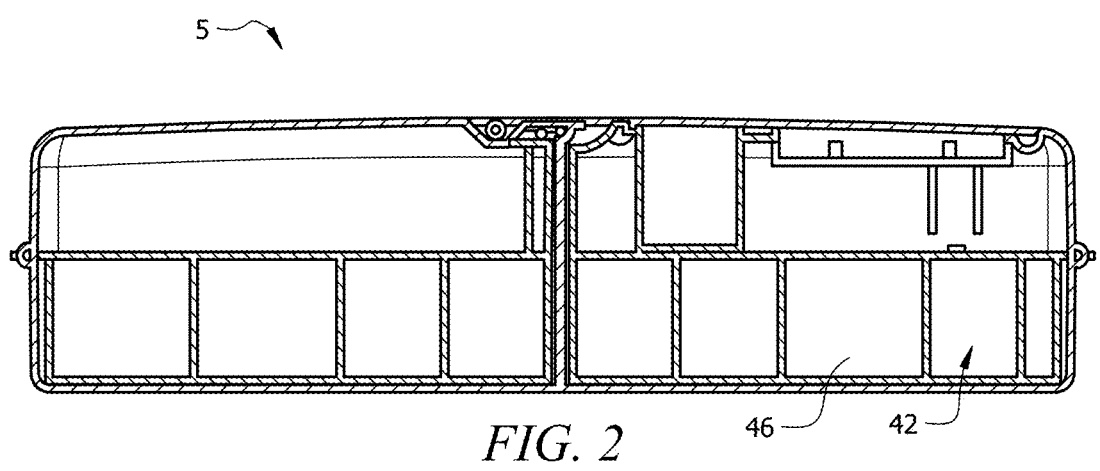
FIG. 2 depicts a cross-section view of the medical supply case viewed from the bottom. Exemplary dimensions are shown for both figures in millimeters.

Referring to FIG. 2 a cross-section view of medical supply case 5 is depicted viewed from the bottom. Partitions, such as partitions 42 and 46 are visible in cross-section throughout the width of the case body. Exemplary dimensions are shown for both figures in millimeters. Dimensions of the cases, cabinets, doors, hinges, and partitions described herein will vary depending on need and configuration. In some embodiments, the dimensions of partitions are approximately 9.5 cm wide by 10.8 cm high by 10.3 cm deep. In some embodiments, the dimensions of the second compartment 40 are approximately 4.0 cm wide by 13 cm high by 5.1 cm deep.

Figure 3A:
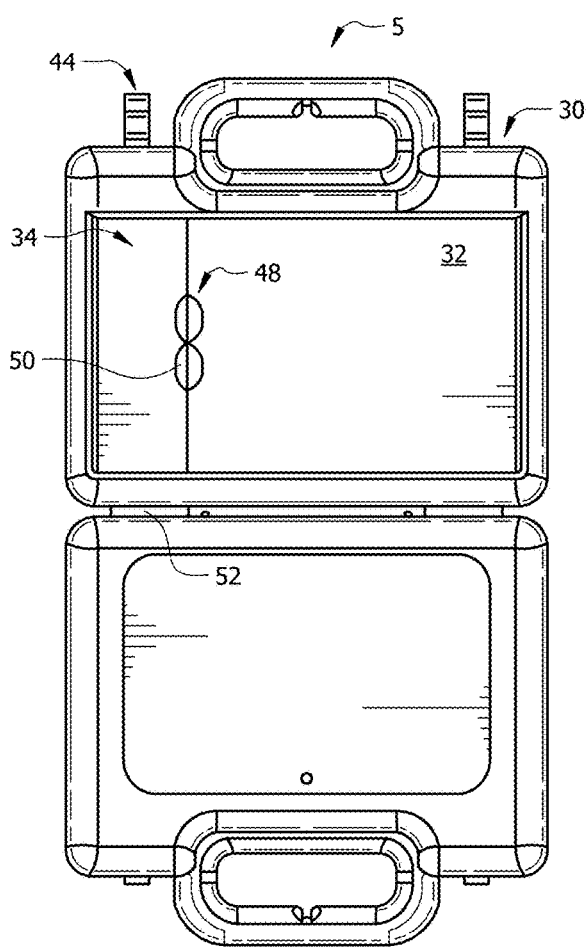
FIG. 3A depicts a non-limiting example of a medical supply case with the case body in an open configuration viewed from the exterior of the case. The first hinged door and the second hinged door are visible in a closed configuration.

Referring to FIG. 3A, in a particular embodiment, shown in an open configuration is the exterior of medical supply case 5 having case body 30. In this embodiment, medical supply case 30 includes a first hinged door 32 in a closed configuration, rendering first compartment 38 containing a bandage application system not visible. Medical supply case 5 also includes second hinged door 34, also shown in a closed configuration, rendering a second compartment not visible. The first hinged door 32 may contain a raised portion 48 to allow a user to quickly open the first hinged door 32. Second hinged door 34 may contain a raised portion 50 to allow a user to quickly open second hinged door 34. As shown in FIG. 3A, the raised portion may align with an indentation on the opposite door. The case body opens by way of a hinge 52 disposed on the bottom side of the case body. The case may also include a clasp 44, which secures the case body 30 in a closed configuration. Two clasps 44 are shown in FIG. 3A. Clasp 44 may be lockable, or it may be relatively easy to open. Clasp 44 may also be a push button, a slide lever, or the like.

Figure 3B:
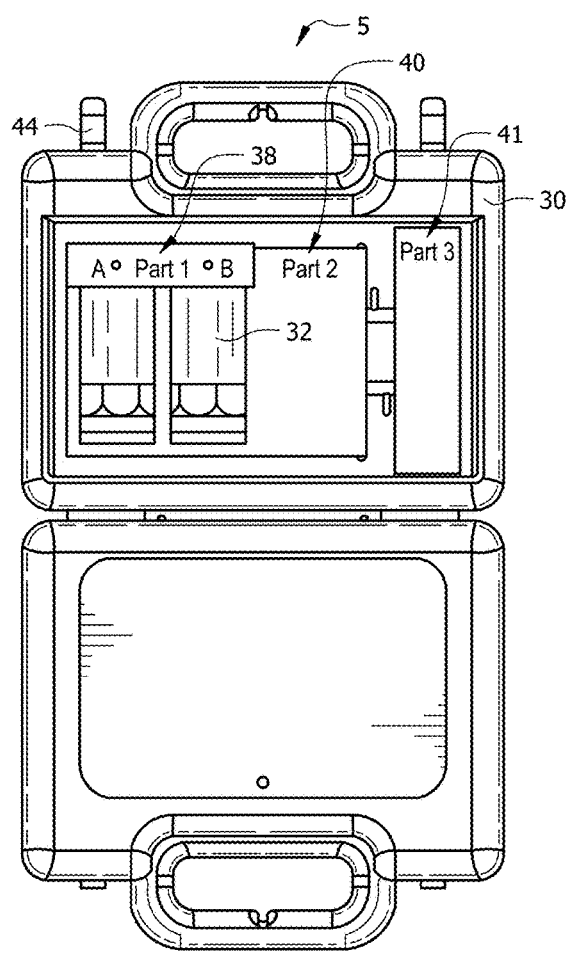
FIG. 3B depicts a non-limiting example of the medical supply case with the case body in an open configuration viewed from the interior of the case. The first compartment containing a bandage application system is visible. The second compartment containing a second medical item is visible, and a third compartment is visible.

FIG. 3B depicts the interior of the medical supply case shown in FIG. 3A in an open configuration. Medical supply case 5 includes first compartment 38 ("Part 1") mounted on the interior of case body 30 and accessible through first hinged door 32. The large arrow in FIG. 3B indicates the direction a user will pull on a bandage in order to remove it from the bandage application system. In some embodiments, the bandage application system is an Easy Access Bandage™ and when a user needs a bandage, the user just pulls down on the bandage in the direction of the arrow. Also visible is second compartment 40 ("Part 2") and third compartment 41 ("Part 3"). In some embodiments, second compartment 40 contains a second medical item. In some embodiments, the second medical item is the same as the first medical item located in first compartment 38. In some embodiments, the second medical item is different than the first medical item located in first compartment 38. In some embodiments, the second medical item is eyewash. In some embodiments, the eyewash is a vial of eyewash. In some embodiments, the eyewash is a bottle of eyewash. The size of the eyewash will vary based on need and configuration. In some embodiments, the eyewash is 1, 2, 3, 4, 5, 6, 7, 8, 9, 10, 11, 12, 13, 14, or 16 ounces. In some embodiments, the eyewash is 16, 32, 48, or 64 ounces. In some embodiments, the eyewash is affixed to the medical supply case. In some embodiments, the eyewash is removable from the medical supply case. In some embodiments, third compartment 41 contains a third medical item. In some embodiments, the third medical item is the same as the first medical item located in first compartment 38 and/or the same as the second medical item located in second compartment 40. In some embodiments, the third medical item is different than the first medical item located in first compartment 38 and/or the second medical item located in second medical compartment 40.

In some embodiments, third compartment 41 contains wipes and creams. In some embodiments, third compartment contains 41 one or more of a plurality of alcohol cleansing pads (such as those for preparation of the skin before injection), antiseptic towelettes (such as those for professional and hospital use; helps prevent infection and allows antiseptic cleansing of face, hands, and body without soap and water), burn cream (first aid to help prevent infection and for the temporary relief of pain and itching associated with minor cuts, scrapes, and burns), triple antibiotic (such as that which helps prevent infections in minor cuts, scrapes, or burns), povidone-iodine prep pads (such as that which provides antiseptic, germicidal skin preparation for minor invasive procedures), hydrocortisone cream (such as that which provides temporary relief of itching associated with minor skin irritations and rashes due to eczema, seborrheic dermatitis, insect bites, poison ivy, poison oak, poison sumac, sores, detergents, cosmetic, and jewelry; other uses of such a product should be only under the advice and supervision of a physician), hand sanitizer (such as that for hand washing to decrease bacteria on the skin), and a plurality of insect sting relief pads (such as that for the temporary relief of pain and itching associated with minor burns, scrapes, and insect bites).

FIG. 3B is configured to contain first compartment 38, second compartment 40, and third compartment 41. Additional compartments can be located on the inside of case body 30 third compartment 41). However, the number of additional compartments will vary according to need and configuration. In some embodiments, the medical supply case or cabinet comprises 1, 2, 3, 4, 5, 6, 7, 8, 9, 10, 11, 12, 13, 14, 15, 16, 17, 18, 19, 20, 25, 30, 35, 40, 45, 50, 60, 70, 80, or 90 compartments. In some embodiments, partitions, for example, partitions 42 and 46, may be configured to be any shape or size. The number of partitions is any number between 1 and 100 compartments. The additional compartments may be configured to securely receive and secure various medical supplies. One or more of the partitions of the third compartment 41 may be removable and replaceable to swap out compartment for larger and/or smaller sizes depending on the dimensions of the medical items) being placed and/or secured within the removable and replaceable third compartment.

The additional compartments of the cases described herein are particularly useful for organizing and securing medical supplies. Medical supplies include supplies useful for the treatment of small cuts and burns, medium cuts and scratches, and severe bleeding and burns. Medical supplies also include supplies useful for emergency preparedness, CPR, disease and injury protection, and instruments. In some embodiments, the third compartment contains one or more of an eye wash, a bandage application system, a plurality of alcohol cleansing pads, a plurality of antiseptic towelettes, one or more packets of burn cream, one or more packets of triple antibiotic ointment, a plurality of povidone-iodine prep pads, one or more packets of hydrocortisone cream, one or more packets of hand sanitizer, a plurality of insect sting relief pads, a first aid guide that provides instructions for identification and initial care of injury and illness, a CPR breathing barrier, one or more sterile dressings, one or more pairs of disposable gloves, one or more bandages, a plurality of aspirin, one or more roller bandages, one or more sterile gauze pads, a triangular bandage, one or more sterile eye pads, one or more vials of sterile eye wash, and a plurality of butterfly wound closures, a roll of first aid tape, a plurality of safety pins, an emergency blanket and a cold pack, a pair of tweezers, a pair of scissors and a plurality of wooden finger splints, a face mask, an emergency poncho, a whistle, a light stick, and an emergency radio/flashlight, and a plurality of batteries.

Figure 4A:
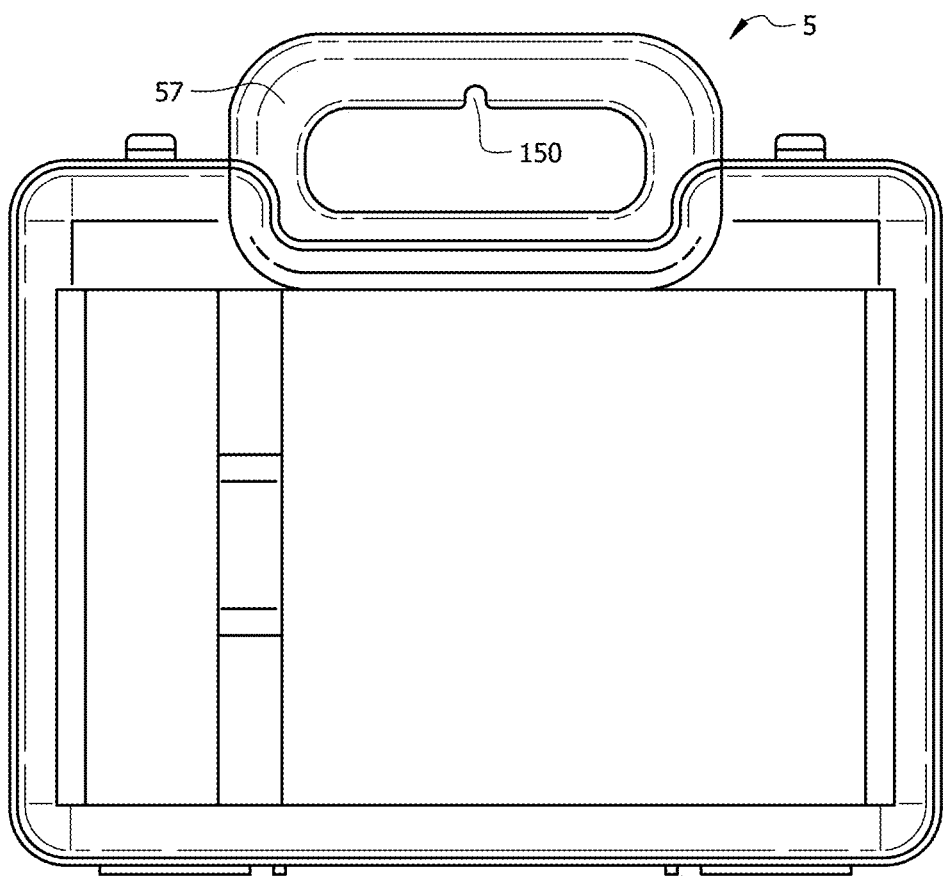
FIG. 4A depicts a cutaway drawing of an exterior view of a non-limiting example of a medical supply case in a closed configuration.
Figure 4B:
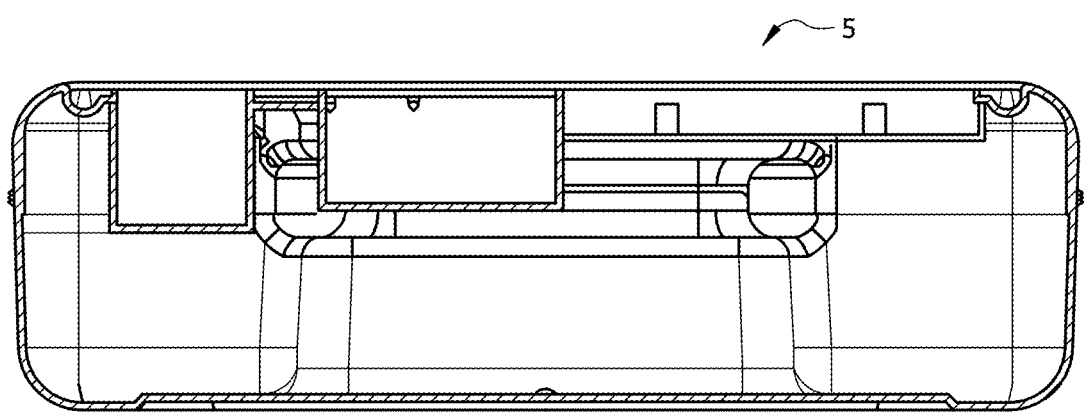
FIG. 4B depicts a cross-section view of the medical supply case viewed from the bottom. Exemplary dimensions are shown for both figures in millimeters.

Referring to FIG. 4A, in a particular embodiment, depicted is a cutaway drawing of an exterior view of a non-limiting example of medical supply case 5 in a closed configuration. In addition, cut out 150 of handle 57 is depicted in FIG. 4A. FIG. 4B depicts a cross-section view of medical supply case 5 viewed from the bottom. Exemplary dimensions are shown for both figures in millimeters. Dimensions of the cases, cabinets, doors, hinges, and the third compartment described herein will vary depending on need and configuration. In some embodiments, the dimensions of the first compartment are approximately 9.5 cm wide by 10.8 cm high by 10.0 cm deep. In some embodiments, the dimensions of the second compartment are approximately 3.0 cm wide by 12.5 cm high by 3.2 cm deep.

Figure 5A:
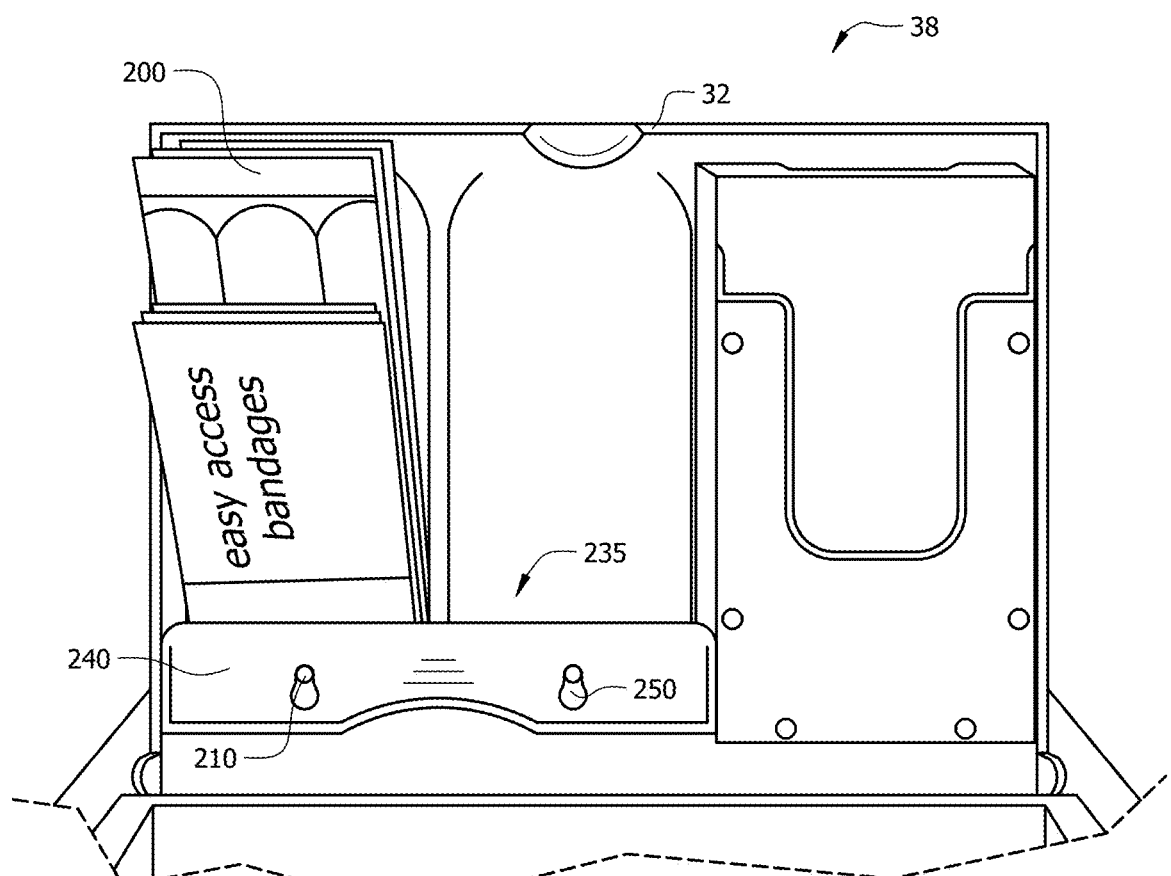
FIG. 5A depicts a front orthogonal view of the first hinged door showing the first compartment with a bandage application system secured in the first compartment by a securing member.
Figure 5B:
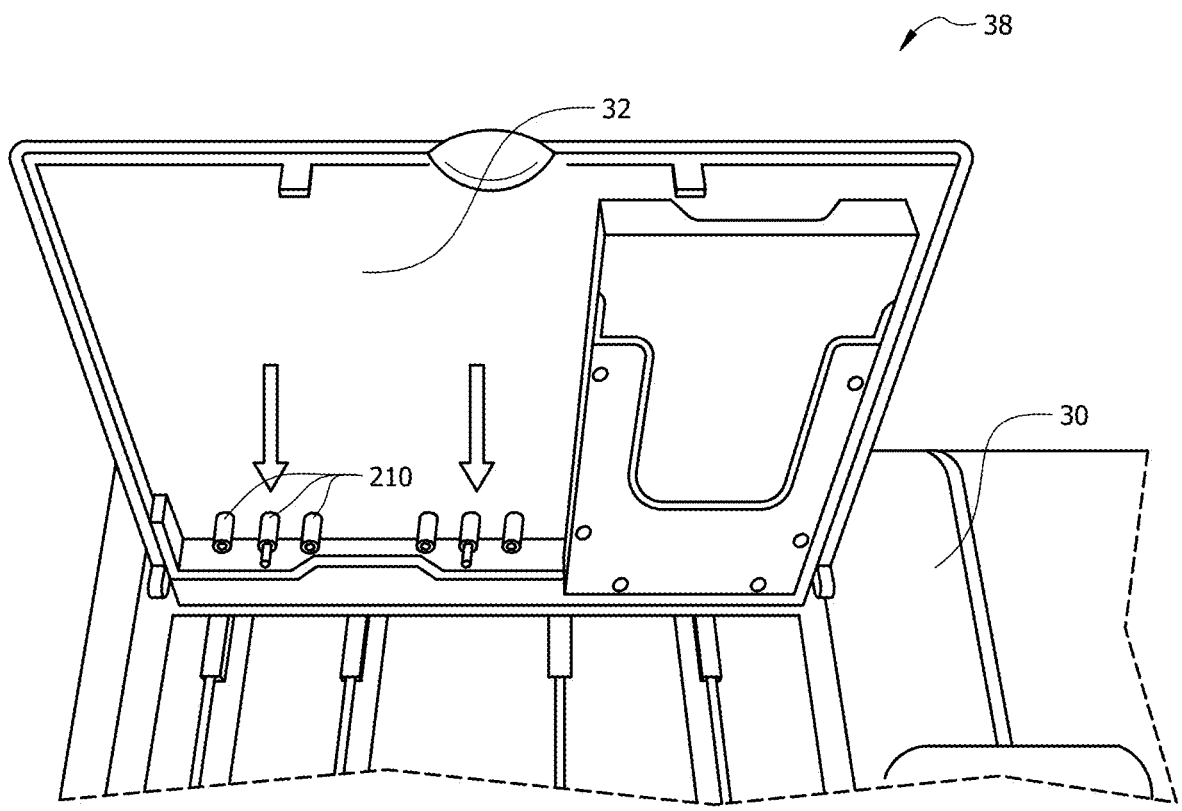
FIG. 5B depicts a top-down perspective view of the first hinged door showing the first compartment and the pegs.

Referring to FIG. 5A, in an embodiment, depicted is a non-limiting example of first compartment 38. First hinged door 32 is disposed on case body 30 and provides access to first compartment 38 which resides within case body. First hinged door 32 may pivot away from case body 30, side out of position, be completely removed, (such as when snap-fitted) or disposed on case body 30 in any manner known in the art that allows access to the first compartment 38 by first hinged door 32. Retaining assembly 235 includes securing member 240 and pegs 210. FIG. 5B depicts pegs 210 protruding from first hinged door 32. Pegs 210 assist in securing the bandage application system to the first hinged door 32.

Retaining assembly 235 is shown in FIG. 5A in the second configuration having bandage application system 200 secured between securing member 240 and first hinged door 32. When retaining assembly 235 is in the second configuration, pegs 210 are disposed through apertures 205 (see FIG. 6) located on bandage application system 200. Disposing pegs 210 through apertures 205 prevents the horizontal and lateral movements of bandage application system 200 and provides resistance when the second end of bandage application system 200 is pulled away from the first end of the bandage application system 200, such that the second end can be dissociated from the first end.

In an embodiment, retaining assembly 235 may be a screw, a clamp, a magnet, an electromagnet, a nail, nuts and bolts, an adhesive, elastic strap, or other securing mechanisms that are known in the art to secure a medical item between securing member 240 and first hinged door 32.

Securing member 240 includes receipts 250 that are configured to receive a portion of pegs 210. Receipts 250 are in mechanical communication with pegs 210 such pegs 210 are at least partially secured within the receipts 250. In an embodiment, receipt 250 is a through-hole having peg 210 insertable through receipt 250 preventing the lateral movement of the first medical item. In an embodiment, receipt 250 is a cantilever hook, snap-fit mechanism, ball and socket, compression hook, compressive traps or beams, bayonet-and-finger snaps, or other connection means that one in the art would appreciate to secure the securing member 240 to pegs 210.

Figure 6:
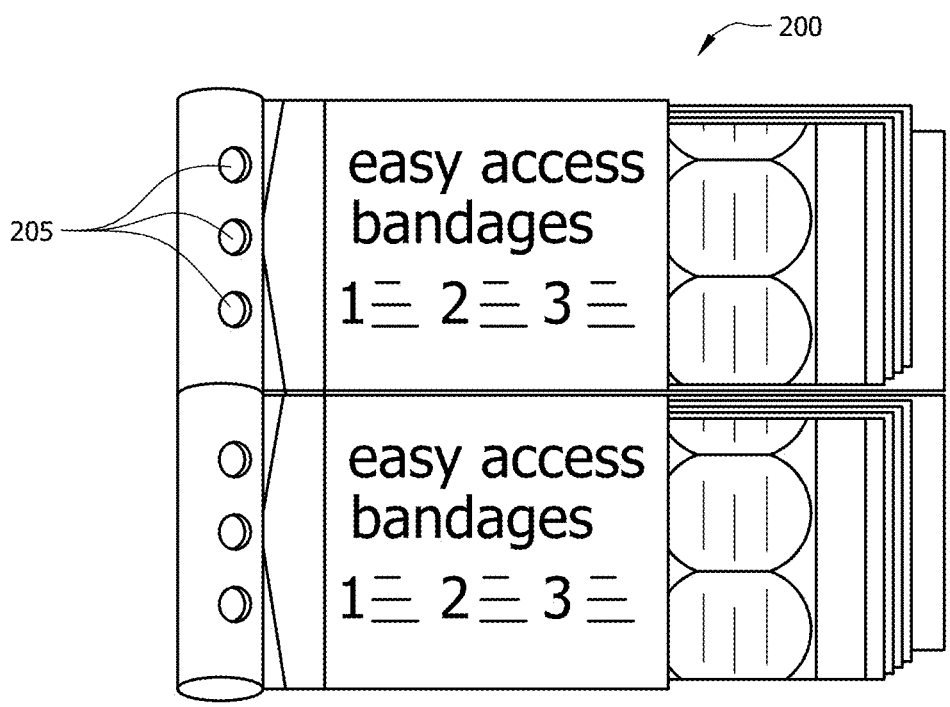
FIG. 6 depicts a perspective view of a bandage application system.

As shown in FIG. 6, bandage application system 200 contains a plurality of apertures 205, In an embodiment, apertures 205 have a diameter slightly larger than the diameters of pegs 210 ensuring pegs 210 can be easily received within the apertures 205. In an embodiment, apertures 205 may be any shape or size that is substantially the same as pegs 210 such that apertures 205 of bandage application system 200 can receive pegs 210 and secure bandage application system 200 between the first hinged door and the securing member. When secured to the first hinged door, pegs 210 are disposed through apertures 205 and pegs 210 are in mechanical communication with the receipts of the securing member thereby securing the bandage application system between the first hinged door and the securing member.

Also described herein, in certain embodiments, are medical supply cases and cabinets comprising a first compartment containing a bandage application system comprising: an individual sterile adhesive bandage; a first wrapper element; and a second wrapper element; whereby the first wrapper element and the second wrapper element at least partially enclose the bandage and are separably in contact to completely enclose the bandage such that when the first and second wrapper elements are pulled in opposite directions the first and second elements separate to partially expose the bandage in a ready-to-apply state.

Also described herein, in certain embodiments, are medical supply cases and cabinets comprising a first compartment containing a bandage application system consisting essentially of: an individual sterile adhesive bandage; a first wrapper element; and a second wrapper element; whereby the first wrapper element and the second wrapper element at least partially enclose the bandage and are separably in contact to completely enclose the bandage such that when the first and second wrapper elements are pulled in opposite directions the first and second elements separate to partially expose the bandage in a ready-to-apply state.

Also described herein, in certain embodiments, are medical supply cases and cabinets comprising a first compartment containing a bandage application system comprising: an individual sterile adhesive bandage; a first wrapper element; and a second wrapper element; the first and second wrapper elements each comprising two parallel sheets sealed on three of four sides to form a pocket, the first wrapper element and the second wrapper element at least partially enclosing the bandage in respective pockets, and the first wrapper element and the second wrapper element separably in contact to completely enclose the bandage.

In some embodiments, the cases and cabinets described herein are a soft pack, a hard pack, or a combination thereof. The interior of the case is optionally accessed by means of a clasp, zippers, clips, hook-and-loop strips, a key/lock, a combination thereof, or the like.

In further embodiments, the cases and cabinets described herein include a first aid guide that provides instructions for identification and initial care of injury and illness. In some embodiments, the first aid guide comprises a series of mini-guides. In other embodiments, the first aid guide is foldable in the same configuration as the third compartment and comprises sections that correspond to the interior compartments. In some embodiments where the cases and cabinets described herein includes a first aid guide, the guide makes specific reference to first aid supplies and equipment contained in the case or cabinet.

In some embodiments, the cases and cabinets described herein include a case or cabinet that is bi-fold, soft-sided, zippered, and made of water-resistant material. In other embodiments, the cases and cabinets described herein include a case or cabinet that is bi-fold, hard-sided, made of plastic, and includes a carrying handle which facilitates wall mounting. A suitable soft pack case is made of a flexible or crushable material that is sufficiently durable and water resistant to protect the medical supplies and equipment from everyday dust and moisture. Suitable materials for a soft pack case include, by way of non-limiting examples, textiles of natural fiber (e.g., cotton, wool, linen, and hemp), textiles of synthetic fiber (e.g., nylon, polyester, aramid, olefin, and acrylic), plastic (e.g., polyvinyl chloride, low-density polyethylene, and polypropylene), rubber, neoprene, silicone, and leather. Suitable materials for a hard pack case include, by way of non-limiting examples, wood, plastic (e.g., polyethylene terephthalate, high-density polyethylene, polyvinyl chloride, polypropylene, high impact polystyrene, acrylonitrile butadiene styrene, and polyamide), metal, and carbon fiber. The cases or cabinets described herein include a means of providing rapid access to the contents of the third compartment to facilitate rapid deployment of the medical supplies. Means of rapid access include, by way of non-limiting examples, clasps, zippers with one slider, zippers with two sliders, hook-and-loop strips, zip-lock closures, slider zipper closures, snaps, ties, buttons, temporary adhesive, latches, and magnets.

In some embodiments, the cases and cabinets described herein are portable, being sized and weighted to facilitate carrying or wearing. In other embodiments, the cases and cabinets described herein are stationary or mounted to an object that is not portable including, by way of non-limiting examples, vehicles, buildings, and natural features of the earth. In some embodiments, the cases and cabinets described herein include a handle that facilitates portability. In further embodiments, the handle includes holes to provide a means to mount the case or cabinet. In some embodiments, the cases or cabinets include holes in the case or cabinet body to provide a means to mount the case or cabinet. In some embodiments, the case described herein is bi-fold, opening in two equal or unequal halves.

In some embodiments, the third compartment of the cases and cabinets described herein contains one or more medical supplies, including first aid supplies, pieces of first aid equipment, emergency preparedness supplies, or emergency preparedness equipment known to those skilled in the art. First aid supplies include, by way of non-limiting examples, adhesive plastic bandages, junior adhesive plastic bandages, knuckle fabric bandages, adhesive spot bandages, fingertip fabric bandages, elbow/knee adhesive bandages, dressings, sterile eye pads, sterile eye wash, sterile saline solution, sterile gauze pads (e.g., 2×2, 3×3, and 4×4), roller gauze bandages (e.g., 3 and 4 inches wide), butterfly wound closure strips, antiseptic wipes, antiseptic towelettes, alcohol cleansing pads, povidone iodine, hydrogen peroxide, insect sting relief pads, cotton-tipped applicators, burn dressings, first aid adhesive tape, combine pads (e.g., 5×9, 8×7¼ and 8×10), triangular bandages, oral medications (e.g., syrup of ipecac, antacid tablets, ibuprofen tablets, acetaminophen tablets, and chewable aspirin tablets), topical medications, and glucose paste or liquid. First aid equipment includes, by way of non-limiting examples, CPR breathing barriers, defibrillators, rescue breathing bags, compressed oxygen, face masks (e.g., paper or cloth), disposable gloves (e.g., vinyl, rubber, plastic, or nitrile, powdered or powder-free), eye protection (e.g., goggles, glasses, or eye shield), hearing protection, scissors (e.g., metal or plastic), tweezers (e.g., metal or plastic), alcohol pads, chemical cold packs, chemical heat packs, hand sanitizer, thermometers (e.g., liquid crystal strips, glass alcohol, or electronic), wooden finger splints, wire splints, and blankets (e.g., cloth, plastic, reflective metalized plastic, or Nomex®). Emergency preparedness supplies and equipment includes, by way of non-limiting examples one or more of the following: face masks (e.g., paper or cloth), eye protection (e.g., goggles, glasses, or eye shield), hearing protection, emergency blankets (e.g., cloth, plastic, reflective metalized plastic, or Nomex®), emergency ponchos (e.g., cloth, plastic, reflective metalized plastic, or Nomex®), chemical light sticks, antiseptic towelettes, triple antibiotic ointment, hand sanitizer, whistles, emergency radios, flashlights, combination radio/flashlights, batteries, water purification tablets, water purification filters, water, and human and animal food.

In some embodiments, one or more supplies or pieces of equipment are useful in providing initial care for one type of injury or illness and are contained in a third compartment of the case or cabinet. In some embodiments, one or more of the supplies or pieces of equipment are useful in providing initial care for more than one particular injury or illness and are contained in more than one partitions of the third compartment of the case or cabinet. In some embodiments, the cases and cabinets described herein contain one instance of one or more particular supplies or pieces of equipment. In some embodiments, the kit described herein contains a plurality of one or more particular supplies or pieces of equipment.

In some embodiments, the partitions of third compartment contains supplies and equipment are organized within the inside of the case or cabinet body to facilitate identification, selection, and acquisition of items appropriate for initial care of a particular illness or injury. In further embodiments, the partitions of the third compartment are completely or partially organized from left to right within the inside of the case or cabinet body in order of increasing severity of the particular illness or injury each partition is stocked to address. In other embodiments, the partitions of the third compartment are completely or partially organized from left to right within the inside of the case or cabinet body in order of decreasing severity of the particular illness or injury each partition of the third compartment is stocked to address. In other embodiments, the partitions of the third compartments are completely or partially organized from left to right within the inside of the case or cabinet body according to the principles of simple triage, advanced triage, or reverse triage. In other embodiments, the partitions of the third compartment are completely or partially organized from left to right within the inside of the case or cabinet body to match the order of topics addressed in a first aid guide or published first aid standards. In still other embodiments, the partitions of the third compartment are completely or partially organized from left to right within the inside of the case or cabinet body to facilitate identification, selection, and acquisition of items appropriate for initial care of illness or injury in a particular setting.

In some embodiments, the partitions of the third compartment include optionally re-sealable closures. Means of opening and re-sealing partitions of the third compartment include, by way of non-limiting examples, adhesive flaps, hook-and-loop strips, zip-lock closures, slider zipper closures, snaps, ties, buttons, magnets, and the like. Re-sealable closures facilitate refilling of spent supplies aftercare is rendered and management of supplies and equipment in multi-illness and/or multi-injury situations. Another aspect of the cases and cabinets described herein is partitions of the third compartment having optional textual labels indicating the particular illness or injury the supplies and equipment therein are useful to treat connected into the partitions of the third compartment. Textual labels include, by way of non-limiting examples, EMERGENCY PREPAREDNESS, SMALL-MEDIUM CUTS AND BURNS, SMALL CUTS AND BURNS, MEDIUM CUTS AND SCRATCHES, SEVERE BLEEDING AND BURNS, CPR EYE, BONE, POISONING, SPRAINS, BITES AND STINGS, PROTECTION, and INSTRUMENTS. In some embodiments, the partitions of the third compartment bear a textual list of supplies and equipment therein. The textual labels and lists are written in one or more languages including, by way of non-limiting examples, Mandarin, Urdu/Hindi, Spanish, English, Arabic, Portuguese, Bengali, Russian, French, Japanese, German, Telugu, Punjabi, Korean, Wu, Javanese, Tamil, Persian, Marathi, Vietnamese, and Italian. In still further embodiments, one or more partitions mounted on an inside of a case or cabinet body bear one or more pictograms depicting instructions for use. The pictograms are graphic symbols that represent an idea or concept and communicate meaning through pictorial resemblance to a physical object or objects.

In some embodiments, the cases and cabinets described herein include a first aid guide that provides instructions for identification and initial care of injury and illness. The guide is written in one or more languages including, by way of non-limiting examples, Mandarin, Urdu/Hindi, Spanish, English, Arabic, Portuguese, Bengali, Russian, French, Japanese, German, Telugu, Punjabi, Korean, Wu, Javanese, Tamil, Persian, Marathi, Vietnamese, Spanish and Italian. In certain of these embodiments, the guide makes specific reference to first aid supplies and equipment contained in the case or cabinet. In further embodiments, the guide includes a symbol or icon that directs the caregiver to particular supplies contained in the cases and cabinets described herein.

In some embodiments, also disclosed herein is a system for refilling a medical supply case that contains a compartment and includes a means of providing rapid access to its contents. Traditional first aid kids lack an effective system to facilitate refill of spent supplies. Without such a system, traditional first aid kits may be improperly refilled and therefore unable to facilitate effective initial care when illness or injuries strike. Without such a system, traditional first aid kits may also be wastefully discarded when depleted of commonly used supplies. There exists a further unrecognized need for a system to easily and consistently refill specific contents of such a medical supply case.

In some embodiments, the cases, cabinets, and systems described herein provide a more cost-effective, more efficient, more consistent, and more accurate means of refilling spent first aid supplies and equipment. Advantages of the systems include but are not limited to prevention of refill errors such as under-filling, over-filling, inconsistent filling, and inclusion of inappropriate items in any particular part of the kit. In some embodiments, the system for refilling a medical supply case is intended for refilling medical supply cases containing a compartment. In some embodiments, the compartment contains a bandage application system. In some embodiments, the bandage application system is configured to fit within the interior compartment of the case. The system further includes a refill kit designed for each compartment. In some embodiments, a refill kit contains a subset of the most commonly used first aid supplies useful in providing initial care for the particular injury or illness. In some embodiments, the refill kit contains all of the first aid supplies useful in providing initial care for the particular injury or illness.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated. As used herein, the term "approximately" or "about" a number refers to that number plus or minus 10% of that number. The term "approximately" or "about" a range refers to that range minus 10% of its lowest value and plus 10% of its greatest value Adhesive Bandage In some embodiments, the cases, cabinets, and systems described herein include an adhesive bandage. Many types of adhesive bandages are suitable. In various embodiments, suitable adhesive bandages include, by way of non-limiting examples, strip bandages, winged bandages, knuckle bandages, fingertip bandages, and the like. Many materials are suitable for an adhesive bandage described herein. In various embodiments, suitable adhesive bandages include, by way of non-limiting examples, plastic bandages, fabric bandages, metal detectable bandages, and combinations thereof. In some embodiments, an adhesive bandage is a non-medicated bandage. In other embodiments, an adhesive bandage is a medicated bandage. In some embodiments, an adhesive bandage is a sterile bandage.

In light of the materials and features described herein, those skilled in the art will recognize that a suitable adhesive bandage is somewhat elastic, flexible, durable, and water-resistant. In some embodiments, an adhesive bandage comprises a backing coated on one side with an adhesive. In some embodiments, a backing is coated on one side with an adhesive to define one adhesive region. In other embodiments, a backing is coated on one side with an adhesive to define a plurality of adhesive regions. In various further embodiments, a backing is coated on one side with an adhesive to define 2, 3, 4, 5, 6, or more adhesive regions. In some embodiments, an adhesive is further suitable for retaining an absorbent pad on the adhesive backing. In further embodiments, the adhesive is pressure sensitive, colorless, and transparent. In some embodiments, an adhesive bandage connects adhesively and reversibly to the skin. In some embodiments, an adhesive bandage described herein includes one or more protective papers overlaying the adhesive region or regions. In further embodiments, a protective paper temporarily overlays an adhesive region to preserve the adhesive region until the time of use. Many materials capable of easy release from the adhesive are suitable for protective papers including, by way of non-limiting examples, plastic and wax paper.

Many sizes are suitable for an adhesive bandage described herein. In some embodiments, an adhesive bandage described herein is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more millimeters long or wide, including increments therein. In some embodiments, an adhesive bandage described herein is about 1, 2, 3, 4, 5, 6, 7, 8, 9, 10, 11, 12, 13, 14, 15, 16, 17, 18, 19, 20, or more centimeters long or wide, including increments therein. In particular embodiments, the adhesive bandages are of the dimensions of 10.2 cm long and 6.4 cm wide; 7.6 cm long and 2.5 cm wide, 7.6 cm long and 1.9 cm wide, 5.7 cm long and 1.5 cm wide and 2.2 cm long and 12 cm wide. In further embodiments, suitable shapes for an adhesive bandage include square and rectangular shaped bandages. In light of the dimensions and features described herein, those skilled in the art will recognize that suitable dimensions include those adapted to facilitate protection, facilitate healing, and lower the risk of infection for of a cut, scrape, puncture, or other wound or lesion, on any part of the human body.

Wrapper Elements

In some embodiments, the bandage application systems described herein include a first wrapper element and a second wrapper element Many materials are suitable for the first and second wrapper elements described herein. In various embodiments, suitable materials for the wrappers include paper, cardstock, plastic, and the like. In further embodiments, suitable materials for the wrappers include materials adapted for containing non-medicated bandages, medicated bandages, sterile bandages, strip bandages, winged bandages, knuckle bandages, fingertip bandages, plastic bandages, fabric bandages, metal detectable bandages, or combinations thereof. In light of the materials described herein, those skilled in the art will recognize that suitable materials are flexible, disposable, and capable of completely enveloping an adhesive bandage, capable of keeping the bandage clean and sterile, suitable for attachment on the interior of the wrapper elements to a protection paper overlaying an adhesive region of the bandage, and suitable for printing instructions on the exterior.

In some embodiments, the two wrapper elements each consist of two parallel sheets of material sealed on three of four sides with adhesive (or other methods of bonding) to create a pocket used to contain an adhesive bandage. In further embodiments, each wrapper element contains one end of the bandage. In still further embodiments, two wrapper elements, each containing one end of the bandage, completely contain the bandage. In some embodiments, the two wrapper elements are separably in contact with one another while completely enveloping an adhesive bandage. In some embodiments, the first and second wrapper elements are the same size and each contain half of an adhesive bandage. In other embodiments, the first and second wrapper elements are different sizes and contain unequal portions of an adhesive bandage.

In some embodiments, the wrapper elements each partially enclose a portion of the adhesive bandage so that when they are separably in contact with one another the entire adhesive bandage is covered and enveloped. In further embodiments, when one element is separated from the other by pulling in opposite directions parallel to the orientation of the bandage, one of the wrapper elements remains associated with the adhesive bandage to facilitate application to the desired area and minimize handling of the bandage prior to application, and the other wrapper element dissociates from the bandage to expose the bandage in a ready-to-apply state.

In some embodiments, one of the wrapper elements remains associated with an adhesive bandage along with a protection paper overlaying a portion of an adhesive region to facilitate handling of the adhesive bandage. In this particular embodiment, users optionally handle the bandage in a ready-to-apply state after exposing part of the adhesive region by the removal of a wrapper element.

In some embodiments, one or more wrapper elements are attached to one or more protection papers such that dissociation of the wrapper element from the bandage removes the one or more protection papers thus exposing one or more adhesive regions. Many methods are suitable for attachment of a wrapper element and a protection paper. In various embodiments, suitable methods include application of adhesive, use of a fastener, and the like.

In a particular embodiment, a wrapper element includes glue applied to connect to a protection paper overlaying an adhesive region on the bandage so that upon removal of the wrapper element, the protection paper overlaying the adhesive region is removed as well.

In some embodiments, the first and second wrapper element, when separably in contact with each other, completely enclose an adhesive bandage. In some embodiments, the first and second wrapper elements are separably in contact with each other without being connected or consisting of one single wrapper. In further embodiments, the first and second wrapper elements are separably in contact via a perforated, scored, or overlapping region. In some embodiments, the first and second wrapper elements are easily and efficiently separated from each other while still completely enclosing the adhesive bandage when in contact with one another. In further embodiments, the first and second wrappers are separable while allowing the adhesive bandage to remain associated with one of the wrapper elements rendering the bandage ready-to-apply. In light of the described separable connection between wrapper elements, those skilled in the art will utilize methods of keeping wrapper element in contact to envelope the adhesive bandage without the elements being fully connected or the elements being rendered one single wrapper.

In a particular embodiment, the wrapper elements are separated from one another without the need to tip or tear the wrapper elements. This particular embodiment demonstrates two wrapper elements forming two separate pockets that together completely envelope the adhesive bandage and are separably in contact to facilitate efficient separation when needed for use. A further embodiment also demonstrates printing designating the appropriate grip areas for proper removal of the wrapper elements in order to access the adhesive bandage.

In some embodiments, instructions are printed directly on the individual wrapper elements, which eliminates the need for printed instructions on the container. Many modes of communication are suitable for the instructions. In various embodiments, printed instructions communicated via words, symbols, pictograms, and combinations thereof. In further embodiments, instructions printed on the individually packaged bandages allow unfamiliar users to follow simple instructions printed on the individual packaging to access a bandage easily without needing to refer back instructions printed on a dispenser or container.

In a particular embodiment, simple and easy to understand instruction are printed outside of the wrapper elements. In combination with the printed markings designating the appropriate grip areas, such instructions allow users to efficiently and rapidly deploy and apply the adhesive bandage.

Operation of the System

In some embodiments, a bandage in a ready-to-apply state includes one or more exposed adhesive regions, an exposed sterile absorbent pad, and an unexposed handling area created by a wrapper element associated with the bandage. In some embodiments, an adhesive bandage described herein is rendered into a ready-to-apply state by a consumer pulling two wrapper elements in opposite directions parallel to the bandage. In further embodiments, pulling two wrapper elements in opposite directions parallel to the bandage separates the wrapper elements and partially exposes the adhesive bandage. In some embodiments, removal of a wrapper element exposes a portion of an adhesive region of the bandage, making it ready-to-apply to skin. In some cases, because a protection paper overlaying an adhesive region of the bandage is connected to a wrapper element, removal of one of the wrapper elements also removes the protection paper allowing the bandage to be applied onto the desired area without further handling (e.g., ready-to-apply). In a particular embodiment, an adhesive bandage is contained and oriented within two wrapper elements such that when one of the wrapper elements is removed, a portion of the bandage remains contained within one wrapper element and the remainder of the bandage is revealed, with an adhesive region exposed, ready to be applied onto the desired area.

In some embodiments, upon separation of the wrapper elements and removal of one of two wrapper elements, a bandage in a ready-to-apply state is rendered about 25, 30, 35, 40, 45, 50, 55, 60, 65, 70, 75, or 80 percent exposed, including increments therein. In further embodiments, upon separation of the wrapper elements and removal of one of two wrapper elements, a bandage in a ready-to-apply state remains about 25, 30, 35, 40, 45, 50, 55, 60, 65, 70, or 80 percent contained within the remaining wrapper element, including increments therein.

In a particular embodiment, an adhesive bandage remains associated with one wrapper element and is in a ready-to-apply state. This particular embodiment demonstrates the efficient application of an adhesive bandage onto a finger while in a ready-to-apply state.

In some embodiments, an adhesive bandage is situated within the wrapper elements so that when a consumer grips the appropriate areas indicated by printing on the wrapper elements, only one end of the bandage will be gripped along with one of the wrapper elements while the other wrapper element is free to be disassociated from the bandage. In further embodiments, an adhesive bandage is situated so that only one end does not extend into a printed grip area of a wrapper element so that during separation of the wrapper elements the user is only gripping a wrapper element without the bandage. In light of the described method of gripping and situating the adhesive bandage within the system, those skilled in the art will recognize orientations of the grip placement and the adhesive bandage within wrapper element(s) that allow the gripping of only one end of the bandage during separation of the wrapper elements.

In some embodiments, an adhesive bandage is situated within wrapper elements having instructions for application that are easily and readily understandable. In further embodiments, an adhesive bandage is situated within the wrapper elements which are printed with graphical and text-based instructions depicting steps necessary to grip both wrapper elements while gripping only one end of the adhesive bandage contained within, partially expose the bandage in a ready-to-apply state, and apply the partially exposed bandage. In light of the described instructions on the wrapper elements, those skilled the art will use instructions that explain how to remove wrapper elements and expose the adhesive bandage in a ready-to-apply state. In certain embodiments, instructions printed on the wrapper elements allow rapid and sterile application of a ready-to-apply adhesive bandage.

Container

In some embodiments, a plurality of the bandage application systems described herein are disposed in a container that defines an interior compartment. In some embodiments, the containers are disposed in a medical supply case or cabinet as described herein. In further embodiments, the bandage application systems are not connected or attached to each other or to the container (e.g., stored loose in a container), which is a substantial departure from traditional bandage dispensers. In still further embodiments, a container serves to preserve the packaged adhesive bandages from the outside environment and maintain the bandages in an efficient and organized manner so that bandages are easily transported, accessed, and utilized. Many types of containers are suitable. In various embodiments, suitable containers include both soft and hard boxes, bags, cartons, and envelopes. A suitable container is made of a wide array of materials. In various embodiments, a container described herein is made of cardstock, cardboard, fiberboard, plastic, nylon, and the like. In light of the disclosure provided herein, a skilled artisan will recognize that suitable materials are sturdy, somewhat rigid, water-resistant, and inexpensive. In certain embodiments, a suitable container is shaped and sized to accommodate the type and number of bandages disposed in the interior.

A container described herein suitably includes a wide range of numbers of bandage application systems. In various embodiments, a container includes about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, or more individual bandage application systems, including increments therein. In various embodiments, a container includes at least 2, at least 5, at least 10, at least 15, at least 20, at least 30, at least 40, at least 50, at least 60, at least 70, at least 80, at least 90, at least 100, at least 200, at least 300, at least 400, or at least 500 individual bandage application systems, including increments therein. In various embodiments, a container includes about 2 to about 10, about 10 to about 20, about 20 to about 30, about 30 to about 40, about 40 to about 50, about 50 to about 60, about 60 to about 70, about 70 to about 80, about 80 to about 90, or about 90 to about 100 individual bandage application systems, including increments therein.

In some embodiments, the container includes multiple individually packaged bandages of the same dimension and type. In other embodiments, the container includes multiple individually packaged bandages of different dimensions and types. In further embodiments, the container includes a variety of bandages. In various embodiments, a container includes about 1, 2, 3, 4, 5, 6, 7, 8, 9, 10, 11, 12, 13, 14, 15, 16, 17, 18, 19, 20, or more types and/or sizes of individual bandage application systems.

Example

The following illustrative example is representative of particular embodiments of the inventions described herein and not meant to be limiting in any way.

A consumer cuts his finger with a sharp knife while chopping vegetables in his kitchen. Knowing that rapid application of a sterile bandage can help to stop bleeding and prevent secondary infection, he immediately goes to a medical supply case mounted on the wall. The medical supply case contains a first compartment accessible via a first hinged door and mounted on the inside of the case body containing a bandage application system as described herein. The consumer quickly opens the first hinged door and pulls downward on one of the bandages contained in the bandage application system. The bandage becomes removed from one of the wrapper elements and half of the bandage is exposed in a ready-to-apply state. The consumer then applies the bandage to cover and protect the wound.

Within a few seconds, the consumer has followed the application instructions and applied the bandage in a sterile fashion with one hand.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A medical supply case comprising:
a first hinged door disposed on a case body and provides access to a first compartment residing within the case body, the first hinged door including:
a peg extend away from the first hinged door from a first end to a second end of the peg;
a securing member having a receipt configured to receive a portion of the second end of the peg, such that the peg and the securing member are coupled with one another at least a portion of the peg resides within the receipt and is at least partially secured within the receipt;
a first medical item secured between the securing member and the first hinged door, the first medical item including:
a first end having an aperture configured to receive at east a portion of the peg, such that the first medical item is retained between the securing member and the first hinged door, thereby preventing the horizontal and lateral movements of the first medical item with respect to the first hinged door,
a second end of the first medical item being detachable from the first end when pulled away from the first end of the first medical item, such that the second end is dissociated from the first end: and
a second hinged door disposed on the case body and provides access to a second compartment residing within the case body.

2. The medical supply case of claim 1, further comprising a third compartment disposed within the case body and inaccessible via the first hinged door.

3. The medical supply case of claim 1, wherein the first medical item further comprises:
an individual sterile adhesive bandage;
a first wrapper element; and
a second wrapper element,
whereby the first wrapper element and the second wrapper element at least partially, enclose the individual sterile adhesive bandage and are different sizes and contain unequal portion of the individual sterile adhesive bandage, and wherein either the first wrapper element or the second wrapper element is attached to an associated protection paper.

4. The medical supply case of claim 1, wherein the receipt is a through-hole.

5. The medical supply case of claim 1, wherein the second compartment is inaccessible via the first hinged door.

6. The medical supply case of claim 1, wherein the first hinged door further includes a raised portion configured to allow a user to transition the first hinged door between an open configuration and a close configuration, wherein when in the open configuration the first compartment is inaccessible to the user.

7. A medical supply case comprising:
a first hinged door disposed on a case body and provides access to a first compartment residing within the case body, the first hinged door including,
a peg extending away from a surface of the first hinged door from a first end to a second end of the peg;
a securing member having a through-hole configured to receive a portion of the second end of the peg, such that when the peg and the securing member are coupled with one another, at least a portion of the peg resides within the through-hole and is at least partially secured with in the though-hole;
a first medical item secured between the securing member and a surface of the first hinged door, the first medical item including:
a first end having an aperture configured to receive at least a portion of the peg, such that the first end of the first medical item is retained between the securing member and the surface of the first hinged door,
a second end being detachable from the first end when pulled away from the first end of first medical item such that the second end is dissociated from the first end;
an individual sterile adhesive bandage at least partially enclosed by a first wrapper element and a second wrapper element, wherein the first wrapper element and the second wrapper element are different sizes and contain an unequal portion of the individual sterile adhesive bandage;
an associated protection paper attached to either the first wrapper element or the second wrapper element; and
a second hinged door providing access to a second compartment residing within the case body, wherein the second compartment is separated from the first compartment by a portion of the case body.

8. The medical supply case of claim 7, wherein a third compartment is disposed within the case body and inaccessible via either the first hinged door or the second hinged door.

9. A medical supply case comprising:
a case body having a first side hingedly coupled with a second side;
a first hinged door disposed on the first side of the case body and provides access to a first compartment residing within the case body, the first hinged door including:
a peg extending away from a surface of the first hinged door from a first end to a second end of the peg;
a securing member having a receipt configured to receive a portion of the second end of the peg, such that when the peg and the securing member are coupled with one another, at least a portion of the peg resides within the receipt and is at least partially secured within the receipt;
a first medical item secured between the securing member and a surface of the first hinged door, the first medical item including:
a first end having an aperture that is configured to receive at least a portion of the peg, such that the first end of the first medical item is retained between the securing member and the surface of the first hinged door;
a second end being detachable from the first end when pulled away from the first end of the first medical item such that the second end is dissociated from the first end; and
a second hinged door disposed on the first side of the case body, wherein the second compartment is separated from the first compartment by a portion of the first side of the case body.

10. The medical supply case of claim 9, wherein the first medical item further comprises:
an individual sterile adhesive bandage;
a first wrapper element; and
a second wrapper element,
whereby the first wrapper element and the second wrapper element at least partially enclose the individual sterile adhesive bandage and are different sizes and contain an unequal portion of the individual sterile adhesive bandage, and wherein either the first wrapper element or the second wrapper element is attached to an associated protection paper.

11. The medical supply case of claim 9, wherein the second hinged door further includes an indentation disposed adjacent to the raised portion of the first hinged door, wherein the indentation assists a user in transitioning the first hinged door between the open configuration and the closed configuration.

12. The medical supply case of claim 9, wherein the medical supply case further includes a clasp configured to secure the first side of the case body to the second side of the case body.

13. The medical supply case of claim 9, wherein a third compartment is disposed within the case body and only accessible to a user when the first side is spaced apart from the second side.

14. The medical supply case of claim 13, wherein the third compartment further includes a plurality of partitions configured to receive one or more additional medical items.

* * * * *